United States Patent [19]

White et al.

[11] Patent Number: 5,610,025
[45] Date of Patent: Mar. 11, 1997

[54] INHIBITION OF INTERFERING ENDOGENOUS ENZYME ACTIVITY IN ASSAYS OF BIOLOGICAL FLUIDS

[75] Inventors: Mark D. White; Wai T. Law, both of Sewell, N.J.

[73] Assignee: Actimed Laboratories, Inc., Burlington, N.J.

[21] Appl. No.: 92,425

[22] Filed: Jul. 16, 1993

Related U.S. Application Data

[63] Continuation-in-part of Ser. No. 828,453, Jan. 31, 1992, abandoned.

[51] Int. Cl.[6] .............................. C12Q 1/37; C12Q 1/26; C12Q 1/51; G01N 33/566

[52] U.S. Cl. .............................. 435/25; 435/23; 435/19; 435/28; 435/7.91; 435/14; 436/501

[58] Field of Search .................. 435/25, 23, 28, 435/10, 14, 19, 7.91, 963; 436/501; 422/56, 57

[56] References Cited

U.S. PATENT DOCUMENTS

| | | | |
|---|---|---|---|
| 3,606,900 | 9/1971 | Gobert et al. | 435/25 |
| 3,862,885 | 1/1975 | Kano et al. | 435/10 |
| 3,907,645 | 9/1975 | Richmond | 435/11 |
| 3,925,164 | 12/1975 | Beaucamp et al. | 435/25 |
| 3,983,005 | 9/1976 | Goodhue et al. | 436/501 |
| 4,328,312 | 5/1982 | Tsurumi et al. | 435/25 |
| 4,656,034 | 4/1987 | Sarnoff | 435/25 |
| 5,055,398 | 10/1991 | Fujie et al. | 435/25 |
| 5,087,556 | 2/1992 | Ertinghausen | 435/7.9 |
| 5,286,626 | 2/1994 | Law et al. | 435/19 |

FOREIGN PATENT DOCUMENTS

| | | |
|---|---|---|
| 0393840 | 3/1990 | European Pat. Off. . |
| 249154 | 9/1987 | Germany . |
| 124394 | 4/1976 | Japan . |
| 138296 | 6/1986 | Japan . |
| 191995 | 8/1986 | Japan . |

OTHER PUBLICATIONS

Barrier, W. R., vol. 45/11–B of Dissertation Abstracts International, p. 3382, 1984. (Abstract).

*Primary Examiner*—Douglas W. Robinson
*Assistant Examiner*—Louise Leary
*Attorney, Agent, or Firm*—Iver P. Cooper

[57] ABSTRACT

The invention describes biological assays in which hydrogen peroxide is used as an oxidizing agent, or wherein hydrogen peroxide is used to oxidize a dye or other intermediate to generate a detectable species. The stability of the hydrogen peroxide in the presence of at least one other enzyme which decomposes hydrogen peroxide is enhanced by the addition of a suitable inhibitor for the enzyme and the inhibitor does not substantially inhibit enzymes used in the assay. When catalase is the enzyme to be inhibited, catalase inhibitors that can be used in the biological systems include hydroxylamine sulfate. The enzyme inhibitor can be incorporated in an integral analytic device.

26 Claims, 1 Drawing Sheet

INHIBITION OF INTERFERING ENDOGENOUS ENZYME ACTIVITY IN ASSAYS OF BIOLOGICAL FLUIDS

This application is a continuation in-part of Ser. No. 07/828,453, filed Jan. 31, 1992, now abandoned, the entire content of which is incorporated by reference.

BACKGROUND OF THE INVENTION

1. Field of the Invention

The present invention is directed to an improvement in the assay art. It relates to methods and compositions for inhibiting endogenous enzyme (e.g., catalase) activity in biological fluids, and more specifically to inhibiting hydrogen peroxide-degrading enzyme activity in biological fluids during qualitative or quantitative analysis of biological fluids, when hydrogen peroxide participates in a signal-generation reaction.

2. Description of the Background Art

Human serum contains many enzymes such as catalase, glutathione reductase and peroxidase, all of which readily decompose hydrogen peroxide to oxygen and water. The most important of these enzymes is serum catalase [EC 1.11.1.6]. The amount of catalase that is present in the plasma of normal human subjects can degrade hydrogen peroxide at a rate of 0.01 to 0.05 moles/liter/minute (Yamagata et al., *Tohoku J. Exp. Med.* 57: 101–107, 1953; Goth et al., *Clin. Chem.* 29: 741–743, 1983). Catalase is also present in erythrocytes in levels 3600 fold higher than in plasma, giving erythrocytes the capacity to degrade gram quantities of hydrogen peroxide over several minutes, Gaetani et al., *Blood* 73: 334–339 (1989).

In fact, catalase has been used to verify the specificity of assays of hydrogen peroxide in plasma or blood, and the degradation of hydrogen peroxide or inhibition of the assay system by the sample should be checked, as catalase present in blood or plasma can reduce the value of measured hydrogen peroxide to zero, Nahum et al., *Free Radical Biology & Medicine* 6: 470–484, 1989.

The ability to measure a wide variety of physiologically active compounds, both naturally occurring and synthetic, has become of increasing importance, both as an adjunct to diagnosis and as therapy. While for the most part assays of physiological fluids and drugs have required clinical laboratory determinations, there is an increasing awareness of the importance of being able to conduct assays in a physician's office and/or in the home. To be able to perform an assay outside of a clinical laboratory setting requires that an assay have a simple protocol and be relatively free of sensitivity to small changes in the condition under which the assay is conducted. Although a number of systems have been developed to try to address the problems associated with analysis outside of a clinical laboratory, there is nevertheless a continuing interest in providing improved and alternative methods to those which are presently generally available.

If a clinical detection reaction requires the presence of hydrogen peroxide at any stage of the assay, any endogenous serum catalase activity present in the reaction system will interfere with the reaction. Dilution of the sample to reduce catalase interference necessarily reduces the sensitivity of the reaction. Many clinical detection systems require the presence of hydrogen peroxide, including determination of cholesterol, triglycerides, glucose, ethanol, lactic acid, etc. For example, when free cholesterol is oxidized by cholesterol oxidase to form cholesteneone and hydrogen peroxide, the hydrogen peroxide so generated can be used to measure the amount of cholesterol originally in the sample.

One of the primary needs in clinical assays is the need to determine cholesterol or triglyceride, including high and low density lipoprotein, levels in blood. There is a clear relationship between total blood cholesterol (mainly the LDL fraction) and coronary artery disease (*Journal of the American Medical Association* 253: 2080–2086, 1985). New guidelines have been established for adults over 20 years of age to identify risk groups associated with blood cholesterol levels, wherein less than 200 mg/dl is a desirable blood cholesterol; 239 mg/dl is borderline high blood cholesterol, and more than 240 mg/dl is considered to be high blood cholesterol and thus the patient is considered to be at high risk.

Because cholesterol levels can be controlled by both diet and cholesterol lowering drugs for those patients at risk, the ability to monitor one's own cholesterol at home for those individuals at risk provides an important tool for monitoring cholesterol levels and thus reducing the potential for heart disease. The ability to measure other naturally occurring compounds of physiological importance, as well as levels of synthetic drugs or hormones, is also of great interest.

Detection of components in liquids, such as cholesterol in blood, by test strips is well known. Vogel et al., in U.S. Pat. No. 4,312,834, and Goodhue et al., in U.S. Pat. No. 3,983,005, disclose test strips which can be used for detecting cholesterol in serum. Problems associated with catalase activity in human serum are avoided by including competing enzymes such as peroxidases in large excess so that the effects of catalase in the sample are minimized.

Allen et al., in U.S. Pat. No. 4,999,287, disclose stripsticks for direct assay of physiologically active compounds such as cholesterol wherein the adverse effects of catalase are lessened by diluting the sample.

In reaction systems where undiluted plasma samples are incorporated, the activity of endogenous enzymes may interfere with an analyte or precursor necessary to measure an analyte of interest. Additionally, many enzymes which are used as reagent in clinical assays may be contaminated with catalase or with other enzymes that destabilize hydrogen peroxide. In chemical reactions that utilize hydrogen peroxide to oxidize a dye or other intermediate to generate a colored or other type of indicator species, the stability of hydrogen peroxide is an absolute necessity in providing an accurate measurement of the analyte of interest.

Enzymes have been incorporated into detergent compositions because of the enzymes' effectiveness against a variety of common stains which are fixed to textiles and laundry. In particular, proteolytic enzymes, which possess the ability to digest and degrade proteinaceous matter, are used to remove from textile proteinic strains such as blood, perspiration milk, cocoa, gravy and other types of sauces. However, many of these detergent compositions also include peroxide and/or persulfate bleaching compounds, and catalase, which is present in many of these common stains, including blood, readily destroys these peroxide and persulfate bleaching compounds.

In order to minimize the effect of catalase on the bleaching compounds, inhibitor compounds can be incorporated in the detergent compositions, as disclosed in Gobert, U.S. Pat. No. 3,751,222; Gobert et al., U.S. Pat. No. 3,606,990, and Oukadi et al., U.S. Pat. No. 4,753,750. The inhibitors may be contacted with the stained cloth during a soaking or prewashing stage prior to contact with the peroxide or persulfate bleaching agent or, alternately, during the washing step, the inhibitors may be included with the peroxide or persulfate bleaching agent. Of particular importance are compositions which comprise a mixture of inhibitor and detergent. These inhibitors are designed to be used in the presence of surfactants, including anionic, nonionic, amphoteric and cationic surfactants in the presence of peroxide and/or persulfate bleaching agents. These bleaching compositions perform best at high pH values, permitting their use in conjunction with common household laundry soaps and detergents.

Among the inhibitors which have been found to be useful in detergent compositions for inhibiting the activity of catalase in soaking or washing solutions are hydroxylamine sulfate; hydroxylamine hydrochloride; phenylhydrazine; hydrazine; hydrazine sulfate; saturated phenols; polyphenols substituted with at least one of $NH_2$, $SO_2NH_2$, Cl, Br, $NO_2$; aminophenols including o-amino-p-chlorophenol; aminotriazoles; alkali metal chlorate; sodium nitride; alkali metal cyanurates; and mixtures of the above.

Many of the above inhibitors used in detergent compositions are active only at extreme pH values, such as at less than 4.0 or greater than 12.0, depending upon the type of detergent and/or bleach composition used. The useful pH range in Gobert et al. is generally from 8 to 11, and preferably from 9 to 10.5. Additionally, many of these compounds are strong reducing agents, such as formaldehyde, which are not compatible with biological assay systems. Others of the inhibitors which are strong oxidizing agents, including alkali metal hypochlorites, alkali metal salts of chlorocyanuric acids, or potassium salts of monopersulfuric acid, may be strong denaturing agents. There properties may be acceptable in detergent formulations, but they are completely unacceptable in clinical assay systems in which the components of the systems are to be preserved, not destroyed.

Additionally, heavy metal salts such as mercuric chloride, nickel salts, or solvents such as acetone, either precipitate proteins or interfere with enzyme activity site activity. Thus, many of these inhibitors cannot be used in diagnostic enzymatic reactions, in which the substances in the samples are not stable at extremes of pH or in the presence of many types of inhibitor compounds.

Many of the conventional tests which require the presence of hydrogen peroxide at some stage of the assay depend upon the use of peroxidase for detection of hydrogen peroxide. However, specific inhibitors for peroxidase include cyanides, sulfides, fluorides, and azides. Therefore, in order to reduce the effects of endogenous catalase in samples from decomposing the hydrogen peroxide to be detected in an assay, it is important not to use catalase inhibitors based upon cyanides, sulfides, fluorides, or azides.

Other workers have inhibited the action of catalase on hydrogen peroxide for different reasons. For example, Fujie et al. in U.S. Pat. No. 5,055,398, disclose a clinical assay for contents of bodily fluid wherein a sample of bodily fluid is first processed with catalase for decomposing hydrogen peroxide that may be present in a fluid sample. That is, catalase is first added to the sample from outside of the system specifically to decompose any hydrogen peroxide that may be present in the sample. Then, because catalase in the sample may interfere with subsequent assays, Fujie et al. add an inhibitor for catalase, such as sodium azide, hydrogen cyanide, hydrogen sulfide, ammonium hydroxide, or 3-amino-1,2,4-triazole, to inhibit the catalase. Unfortunately, many of these inhibitors, including hydrogen cyanide, hydrogen sulfide, and sodium azide are compounds which have been found to decompose horseradish peroxidase, so that the Fujie et al. method is limited in use to those assays which do not subsequently use peroxidase.

It is also known that different peroxidase isoenzymes are inhibited to different degrees by inhibitors, Kay et al., *J. of Biol. Chem.*, 242 (10): 2470–2473, 1967. Thus, the inhibitory effect of an enzyme inhibitor may vary depending upon the particular isoenzyme used, and may also vary depending upon the reaction milieu.

Beaucamp et al., in U.S. Pat. No. 3,925,164, disclose a method for determination of cholesterol by using catalase as a reagent to detect hydrogen peroxide formed by treating cholesterol with cholesterol oxidase. In this case, catalase is added as a reagent for detecting hydrogen peroxide formed; there is certainly no reason that catalase would be considered to interfere with the assay reactions in this case, as the catalase is used as a reagent.

Kano et al., in U.S. Pat. No. 3,862,885, teach a process for determining uric acid in a blood sample with uricase using a catalase inhibitor such as sodium azide. As discussed above, however, use of sodium azide to inhibit the action of catalase precludes later use of peroxidases in the assay. Since many clinical assays depend upon the production or use of hydrogen peroxide with peroxidase, the use of sodium azide to inhibit catalase introduces other errors into the assay.

No admission is made that any of the background references cited above constitute prior art or pertinent prior art.

SUMMARY OF THE INVENTION

It is an object of the present invention to overcome the aforesaid deficiencies in the background art.

It is a further object of the present invention to provide compositions for analysis of physiological fluids which are not inactivated in the reaction milieu by enzymes which decompose hydrogen peroxide.

It is another object of the present invention to provide compositions for analysis of physiological fluids which are not inactivated by catalase present in the physiological fluids.

It is still another object of the present invention to provide compositions for the analysis of physiological fluids which are not inactivated by catalase present in the reagents.

It is a further object of the present invention to minimize the adverse effects of catalase in an analysis system in which hydrogen peroxide is generated.

It is still another object of the present invention to minimize the adverse effects of catalase in reaction systems in which hydrogen peroxide is generated in serum in the absence of competitive enzymes such as peroxidases.

According to the present invention, inhibitors of enzymes which decompose hydrogen peroxide are used in clinical assays in which hydrogen peroxide is either present in the sample or is subsequently generated during the course of the assay. For example, the hydrogen peroxide may be used as an oxidizing agent, e.g., to oxidize a dye or other intermediate to generate a detectable species. These inhibitors may be provided in order to maintain the stability of the hydrogen peroxide.

Thus, for example, the addition of inhibitors of catalase or other such enzyme activity permits the use of undiluted plasma or serum in a diagnostic device without loss of the presence of hydrogen peroxide. Furthermore, the concentration of the inhibitor substance is sufficiently low and/or the activity of the inhibitor is sufficiently specific so that it does not interfere with the concomitant chemical (including enzymatic) reactions that determine the concentration of analyte present.

The present invention is particularly advantageous in that undiluted serum or plasma samples may be used for the determination of analyte concentration. This is particularly important when the reaction format is such that hydrogen peroxide generated in serum or plasma samples may be used for the determination of analyte concentration. This is particularly important when the reaction format is such that hydrogen peroxide is generated in serum or plasma samples in the absence of competitive enzymes such as peroxidases. Most importantly, the inhibitors are effective inhibitors of catalase activity while not interfering with enzymatic end point detections, including the Trinder type of enzymatic end point reactions for the quantitative measurement of cholesterol or triglycerides where the production of a visually detectable product species is proportional to the concentration of analyte in the sample.

In a preferred embodiment, hydroxylamine salts such as hydroxylamine sulfate and hydroxylamine hydrochloride are used to inhibit catalase activity. These compounds provide excellent inhibition of catalase activity in serum when the inhibitors are present in very low concentration, e.g., in the range of about 0.5–40.0 mM in the reaction solution. Moreover, these inhibitors do not interfere with the several commonly used reporter enzymes which may be present in the system, including cholesterol esterase and cholesterol oxidase, and, for all practical purposes, horseradish peroxidase. Thus, the presence of the hydroxylamine salt does not interfere with the course or the result of the reaction. This reaction format is particularly advantageous because catalase interference is eliminated before the subsequent reaction steps occur, thus permitting an accurate determination of the analyte of interest.

The invention encompasses all compounds which effectively inhibit activity of endogenous enzymes while not interfering to a discernible amount with the assay to be conducted. While hydroxylamine salts are the preferred compounds, one skilled in the art, using the tests described herein to determine enzyme inhibition and lack of interference with the assay, can readily determine other compounds which can be used as endogenous enzyme inhibitors for biological assays and which come within the purview of the present invention.

DETAILED DESCRIPTION OF THE INVENTION

Figure 1:
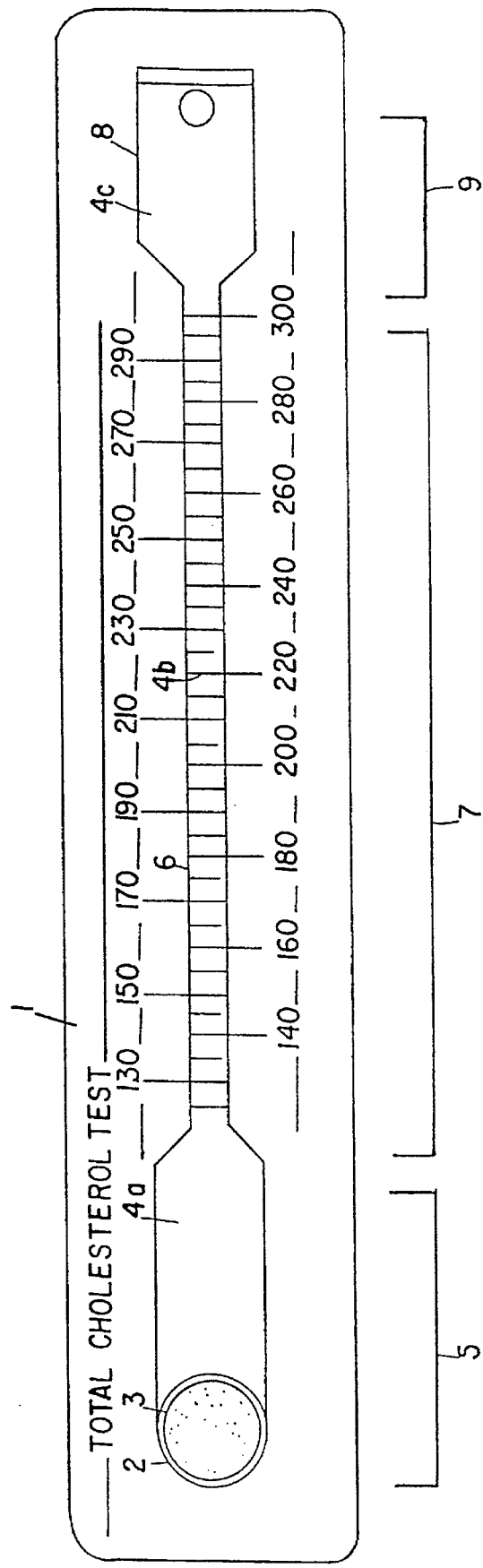
FIG. 1 illustrates a side view of the self-contained analyzer.

This invention pertains generally to the assay use of inhibitors of enzymatic decomposition or conversion of hydrogen peroxide which do not substantially interfere with other enzymes in the assay system, including analytes, binding agents and labels.

In a preferred embodiment, the inhibitors are catalase inhibitors. The catalase inhibitors used in the present invention should more strongly inhibit the action of catalase but not of other important enzymes used in clinical assays, such as peroxidases, cholesterol esterases, etc. Preferably, the other enzymes are not substantially inhibited, and the inhibitors do not substantially interfere with the assay reactions to be conducted.

As is well understood, "substantial inhibition" means that the action of catalase is inhibited to such an extent that there is no discernible interference with the assays conducted. In other words, sufficient catalase is inhibited so that hydrogen peroxide present in the reaction system is not destroyed by catalase present in the reaction system. More specifically, one can determine an inhibitory amount of the inhibitor by choosing a starting dosage, measuring the degree of inhibition of both catalase and other enzymes in the assay system, and then increasing or decreasing the dosage of inhibitor accordingly. The amount of inhibition achieved generally must be above about 90% to be useful in reducing interference from catalase.

Likewise, one skilled in the art can readily determine if the peroxidase or other enzyme used in the clinical assay is "substantially inhibited" by the catalase inhibitor. A reaction with the enzyme can be conducted both in the presence and in the absences of the catalase inhibitor to ascertain if the inhibitor is active against the enzyme used for the assay.

Applicants have developed an assay for catalase inhibition which permits the ready identification of catalase inhibitors. This screening assay is readily adapted to identification of inhibitors of other hydrogen peroxide inactivating enzymes. It is believed that the mechanism of catalase activity inhibition by the hydroxylamine compounds is that of competitive inhibition of the catalase activity (However, applicants are not bound to this theory, and their invention is not limited to inhibitors which so function).

Compounds having structures similar to hydrogen peroxide were initially screened for catalase inhibition in clinical assay systems using samples of aqueous hydrogen peroxide containing additional catalase along with a dye indicator/peroxidase system. The inhibitors were added along with the extra catalase, and spectrophotometric measurements at 514 nm were obtained.

The percent recovery of absorbance is defined as follows:

$$\% \text{ Recovery of absorbance} = \frac{\text{Absorbance inhibition solution}}{\text{Absorbance blank solution}} \times 100\%$$

In the following tables, the concentrations of inhibitor substances are expressed as the final concentration in the reaction system after accounting for dilution factors.

TABLE I

| Reagent Format | Inhibitor Concentration (mM) | % Recovery |
|---|---|---|
| A. Peroxide samples | | |
| 1. Peroxide w/o catalase | 0 | 100 |
| 2. Peroxide with catalase Adding: | 0 | 18 |
| 1) Hydroxylamine HCl | 0.5 | 96 |
| | 5 | 95 |
| | 10 | 91 |
| | 20 | 92 |
| | 40 | 92 |
| 2) Hydroxylamine sulfate | 0.5 | 99 |
| | 5 | 95 |
| | 10 | 90 |
| | 20 | 97 |
| | 40 | 91 |
| 3) 4-Chlorophenol | 0.5 | 37 |
| | 5 | 50 |
| | 40 | 84 |

TABLE I-continued

| Reagent Format | Inhibitor Concentration (mM) | % Recovery |
| --- | --- | --- |
| 4) Resorcinol | 0.5 | 50 |
|  | 5 | 57 |
|  | 40 | 79 |
| 5) Nickel (II) chloride | 5 | 60* |
| 6) Cupric nitrate | 5 | 85* |
| 7) Sodium formate | 40 | 8 |
| 8) Sodium azide | 40 | 109 |
| 9) Sodium nitrite | 40 | 30 |
| 10) Sodium fluoride | 40 | 7 |
| 11) Methanol | 2% | 7 |
| 12) Ethanol | 2% | 6 |
| B. Cholesterol samples | Reporter System: | Primaquine/MBTH |
| 1. Aqueous 50 mg/dL w/o catalase | 0 | 100 |
| 2. Aqueous 50 mg/dL with catalase | 0 | 5 |
| Adding: |  |  |
| 1) Hydroxylamine sulfate | 0.5 | 96 |
| 2) Hydroxylamine HCl | 0.5 | 98 |
| 3. Plasma with catalase | 0 | 15 |
| Adding: |  |  |
| 1) Hydroxylamine sulfate | 0.5 | 99 |
| 2) Hydroxylamine HCl | 0.5 | 98 |

*Precipitation occurred

As noted above, in order to be useful in a clinical assay, an inhibitor should ideally inhibit catalase activity more than about 90%. Although several compounds other than the hydroxylamine salts are shown to be good inhibitors of endogenous enzymes, these compounds cannot be used with horseradish peroxidase, one of the most commonly used enzymes in clinical assays is hydrogen peroxide. Therefore, the inhibitors which inhibit horseradish peroxidase, including cyanides, sulfides, fluorides, and azides, cannot be used for assays requiring the use of horseradish peroxidase, as these inhibitors interfere with the hydrogen peroxide reaction with horseradish peroxidase, resulting in an erroneous determination.

Preferably, for a particular assay system, use of a particular inhibitory amount of an inhibitor for endogenous enzymes achieves at least a 90% recovery in absorbance relative to the same system without the inhibitor. More preferably, it is at least 95%, and still more preferably, it is at least 97%.

It is desirable that the inhibitor be substantially more specific for the catalase or other contaminant enzyme than for the competing enzymes (e.g., analytes, binding agents, or reporter enzymes). Preferably, the degree of inhibition of the contaminant enzyme is at least 50% greater than the degree of inhibition of the competing enzymes. More preferably, it is at least twice as great.

Table 1 shows the results of inhibitor screening experiments performed on potential inhibitors of catalase using a variety of reaction formats. For both peroxide samples and cholesterol samples, Table 1 illustrates that the hydroxylamine compounds and sodium azide are the most effective inhibitors of catalase activity. However, as noted above, sodium azide is not particularly useful for clinical assays because of its inhibition of one of the most commonly used enzymes in these assays, horseradish peroxidase.

It should also be noted that, in most instances, the recovery of absorbance with the hydroxylamine compounds is greater than 95%, and in a preferred embodiment, the inhibitor provides at least this degree of recovery. The screening assay may be extended by determining the effect of these inhibitors on other enzymes whose function is important to the ultimate assay in addition to horseradish peroxidase.

The hydroxylamine salts have been found to change absorbance at the peak to a very slight degree, providing additional evidence that these compounds do not interfere with the reactions sought to be detected. In contrast hereto, sodium azide at the same concentrations changes the absorbance to a much greater extent, thus lessening its vitality in assays which use absorbance for quantative determinations.

TABLE II

| Concentration of Inhibitor | Δ Abs at the Soret Peak $\lambda = 414$ nm |
| --- | --- |
| Hydroxylamine HCl |  |
| 5 mM 0.075 | 0.075 |
| 29 mM | 0.037 |
| 50 mM | 0.076 |
| Sodium Azide |  |
| 5 mM | 0.033 |
| 29 mM | 0.512 |
| 50 mM | 0.438 |

The inhibitors of the present invention can be incorporated into any reagent system for use wherein hydrogen peroxide is generated in serum in the absence of competitive enzymes such as peroxidases; however, peroxidases can be added subsequent to the generation of hydrogen peroxide with no interference. Of particular importance are assays for cholesterol or triglycerides, such as those disclose in U.S. Pat. Nos. 4,312,834 and 3,983,005, both of which patents are incorporated herein by reference. Additional assays which depend upon the generation of hydrogen peroxide include enzymatic assays for glucose, uric acid, lactic acid, free fatty acids, glutamate-pyruvate transaminase, glutamate-oxaloacetate transaminase, creatine phosphokinase, lactate dehydrogenase, cholinesterase, creatinine and the like.

The inhibitors of this invention are employed in an inhibitory amount, i.e., in an effective amount to inhibit the action of endogenous enzymes in the sample. This effective inhibitory amount is determined by choosing a starting dosage of the inhibitor, measuring the degree of inhibition of endogenous enzymes in the assay system, and then increasing or decreasing the dosage accordingly. The amount of inhibition achieved usually needs to be above about 90% to be useful in reducing interference from endogenous enzymes. The inhibitor may be added directly to the sample, or first to a reagent employed in the assay. The inhibitor may be added before the assay begins, or after the addition of one or more reagents, but of course is preferably added before catalase has the opportunity to act on hydrogen peroxide present in the assay system.

Another advantage of the hydroxylamine salts for use in clinical assays is that they do not lyse red blood cells, whereas some of the other inhibitors for catalase have been found to lyse red blood cells. Although most quantitative assays require that the red blood cells first be removed from a blood sample before the assay is initiated, occasionally a few red blood cells remain in the sample. If these red blood cells are lysed by any of the reagents in the reaction mixture, there can be a great interference with absorbance of the reaction mixture, resulting in an invalid test.

Other endogenous enzymes which act on hydrogen peroxide and which may be desirable to suppress in an analytic environment include superoxide dismutase, glutathione peroxidase and glucose-6- phosphate dehydrogenase. Accordingly, the enzyme inhibitor may be chosen to inhibit one or more of these enzymes selectively, using the tests as described above to determine if there is substantial inhibition (about 90%) of the enzyme. The inhibition of the enzyme should be selective for the environmental enzyme relative to an assay enzyme, i.e., it should inhibit the enzyme of interest at least 50% more than any of the enzymes used in the assay.

If there are several enzymes which it is desirable to suppress, one may employ a single inhibitor which substantially inhibits all of them (but does not intefere with the assay), or separate inhibitors for each enzyme, or anything in between.

Example 1

This example provides an example of quantitative determination of cholesterol in whole blood, using a device such as disclosed in Ser. No. 07/352,985, filed May 17, 1989, which application is incorporated herein in its entirety by reference.

The device of Ser. No. 352,985, now U.S. Pat. No. 5,087,556, is a self-contained chromatic quantitative analyzer for quantitatively detecting an analyte in a biological fluid. The device includes a base having a first open reservoir for receiving the sample, with a means for separating solids from the sample in the first open reservoir. A channel draws, by capillary and/or wicking action, the sample from the first open reservoir to a second open reservoir. The second open reservoir draws the biological fluid form the channel and, when the second open reservoir is filled with the sample, the capillary and/or wicking action terminates. A membrane is provided in the channel which is permeable by the sample. There is at least one chromatic chemical indicator immobilized in the membrane in a predetermined concentration.

The chromatic chemical indicator detects the analyte of interest, a reaction product of the analyte, or a labelled analogue developing a color. The colored portion of the channel caused by reaction of the chromatic chemical indicator with the analyte, or a derivative thereof, as observed after the capillary action is terminated, corresponds to the concentration of the analyte in the biological fluid. A scale is provided along the channel so as to equate the colored portion of the channel to the concentration of analyte.

The device is illustrated in FIG. 1. The device 1 includes a first open reservoir 2 containing a means for separating suspended solids 3 from a biological fluid. The means for separating solids 3 is a porous material such as fiberglass, paper, porous plastic or other material having an appropriate mesh and which allows the sample to pass rapidly. The means for separating solids can also include chemical additives to assist in retarding the movement of the suspended matter. The means for separating solids 3 must prevent the majority of solids, such as red cells, from leaving the first open reservoir 2. The liquid phase of the filtered biological fluid is drawn by a membrane 4 through an initial reaction zone 5. The membrane 4a of initial reaction zone 5 can be a porous material into which reagents required for a first reaction step have been incorporated. The incorporation of these reagents can be performed by a variety of physical or chemical processes. These processes can include saturating the porous material with a liquid reagent solution followed by drying, or by forming the porous material by coating particles of an insoluble material with the reagents and subsequently suing a mass of the coated particles as a porous matrix. Additionally, the porous material can be formed by covalently bonding the chemicals or biologicals of interest to a chemically activated porous matrix.

The channel 6 leads from the first open reservoir 2 which includes the initial reaction zone 5 in one embodiment. The channel 6 contains the membrane 4 discussed above. The membrane 4 can be of the same or different material as the membrane 4a used in the initial reaction zone 5. The channel 6 containing membrane 4b forms a chromatic reaction zone 7 wherein the point between reacted and unreacted chromatic chemical indicator (not shown) corresponds to a concentration of analyte in the sample. A sample of a scale is shown along channel 6 which corresponds to the point between reacted and unreacted chromatic chemical indicator to a concentration of analyte in the sample.

The chromatic reaction zone 7 of the quantitative test device 1 contains the membrane 4b. Membrane 4b can be a fiber, a membrane strip, or another elongated body containing a predetermined, precise amount of immobilized dye or chromatic chemical indicator. This dye changes color upon either direct interaction with the analyte of interest or indirect interaction with a derivative thereof that is generated or added in the initial reaction zone 5. The relative volume of filtered sample that is contained in the channel 6 is small when compared to the volumes of sample in the first open reservoir 2 or the second open reservoir 8.

The second open reservoir 8 provides a means for metering the flow and volume of biological fluid through the channel 6. The second open reservoir 8 contains a membrane 4c. Membrane 4c is a porous material with a high absorptive activity and the ability to absorb rapidly and contain a precise volume of sample. The membrane 4c can be an extension of the membrane 4b or can be another material. The second open reservoir 8 must be partly visible to the user and, desirably, changes color when it is completely saturated with liquid. This provides an optional but very desirable third reaction zone 9. When sufficient biological fluid enters the first open reservoir 2, it eventually fills the second open reservoir through capillary and/or wicking action. This condition indicates that the capillary and/or wicking action is terminated and the test results are to be read. Membranes can contain reagents to stabilize the reactants or to reduce interferences with reading the optical scale.

The following enzyme reagent was prepared for application to a membrane channel:

|  | General Range | Preferred Composition | Approximate amount per strip area ($m^2$) |
|---|---|---|---|
| cholesterol esterase | 100–1500 U | 600 U | 6000 U |
| cholesterol oxidase | 100–1500 U | 400 U | 4000 U |
| sodium cholate | 1–50 mg | 10 mg | 100 mg |
| ascorbic acid oxidase | 10–500 U | 100 U | 1000 U |
| Triton X 100 | 1–100 μL | 10 μL | 100 μL |
| Potassium hydrogen phosphate | 0.1–0.6 g | 0.3 g | 3 g |
| disodium hydrogen phosphate dihydrate | 0.1–0.6 g | 0.85 g | 8.5 g |
| deionized water | 10 ml | 10 ml | |

| | General Range | Preferred Composition | Approximate amount per strip area (m²) |
|---|---|---|---|
| hydroxylamine sulfate | 0.001–100 mg | 1 mg | 10 mg |

The following dye reagents were prepared for application to the channel:

| | General Range | Preferred Composition | Approximate amount per strip area (m²) |
|---|---|---|---|
| Primaquine phosphate cellulose | 1–10 g | 4 g | 40 g |
| MBTH 3-Methyl-2 benzotiazolinone hydrazone hydrochloride hydrate | 5–40 mg | 30 mg | 300 mg |
| Polyvinyl alcohol | 1–3 g | 1.5 g | 15 g |
| peroxidase | 1000–50,000 U | 10,000 U | 100,000 U |
| potassium dihydrogen phosphate | 0.1–0.6 g | 0.3 g | 3 g |
| disodium hydrogen phosphate dihydrate | 0.1–1.5 g | 0.85 g | 8.5 g |
| polyvinyl pyrrolidone or Triton X 100 | | 0.05 ml | 0.5 ml |

Example 2

This example shows the effect of hydroxylamine salts on the length of color bar formed, which indicates the quantity of cholesterol in the sample. The results are shown in the following table.

| Plasma Cholesterol | Color Bar without HA | Length with HA |
|---|---|---|
| 200 mg/dL | 0 cm | 2.3 cm |
| 400 mg/dL | 0 cm | 4.9 |

Example 3

The following example illustrates the reagents necessary to manufacture devices for quantitatively analyzing triglycerides in whole blood:

| | General Range | Preferred Composition | Approximate amount per strip area (m²) |
|---|---|---|---|
| glycerol kinase | 100–10,000 U | 2000 U | 20,000 U |
| lipase | 500–100,000 U | 10,000 U | 100,000 U |
| glycerol phosphate oxidase | 100–50,000 U | 12,000 U | 120,000 U |
| ATP | | 40 μmole | 0.4 μmole |
| Triton X100 (surfactant) | | 20 μL | 200 μL |
| Magnesium sulfate | | 20 μM | 0.2 mM |
| NaCl | | 200 μM | 2 mM |
| Pipes buffer | | 50 μM | 0.5 mM |
| Sodium azide | | 1 mg | 10 mg |
| Deionized water | | 10 mL | |

The device prepared from the above formulation is used in the same manner as in Example 1.

Example 4

| | General Range | Preferred Composition | Approximate amount per strip area (m²) |
|---|---|---|---|
| glucose oxidase | 100–30,000 U | 6,000 U | 60,000 U |
| citric acid | 0.01–1 g | 0.3 g | 3 g |
| sodium citrate | 0.1–2 g | 1.0 g | 10 g |
| hyroxylamine hydrochloride | 0.1–10 mg | 1.0 mg | 10 mg |
| deionized water | | 10 mL | |

The device prepared from the above formulation is used in the same manner as Example 1.

The enzyme inhibitors of the present invention can be used with any type of clinical assay in which hydrogen peroxide is produced or where hydrogen peroxide is present in the sample or in the reagent. Use of the enzyme inhibitors thus eliminates any uncertainty that may be present in the assay because of environmental enzyme destruction of hydrogen peroxide.

Although the enzyme inhibitor of the present invention can be used in any type of assay in which hydrogen peroxide is either present or generated, integral analytic elements incorporating a reagent layer are particularly useful for diagnostics, and the enzyme inhibitor can readily be incorporated in these elements.

The inhibitors of the present invention can be used with any type of reagent which is currently used for clinical assays which produce hydrogen peroxide as a reaction product, or in which hydrogen peroxide is otherwise present. For example, in cholesterol assays, reagents which hydrolyze cholesterol esters contained in a liquid sample, which decompose cholesterol, including cholesterol liberated by such hydrolysis, and to provide detectable changes related to the total cholesterol content of the liquid all can be used along with the enzyme inhibitors of the present invention, with no adverse effects on the reaction.

Since the enzyme inhibitors are to be used in clinical assays, they must be active at the pH's used for these assays. Blood, which is an excellent buffer, has a pH of about 7.2. Most clinical assays are conducted at about this pH, generally from about 7.0 to slightly below about 8.0, although clinical assays can be conducted at a pH range from about 4.5 to about 8.0 For optimum results, the pH is from about 7.0 to below 8.0. Therefore, the enzyme inhibitors must be active at these pH ranges.

For cholesterol quantification in aqueous solutions containing cholesterol and/or cholesterol esters, such as blood serum, indicators can be used which quantify the level of hydrogen peroxide generated in the oxidation of cholesterol.

Indicator compositions for the detection of enzymatically generated hydrogen peroxide are well known in the art, particularly as indicator compositions in the enzymatic detection of glucose and uric acid. U.S. Pat. Nos. 3,092,465 and 2,981,606 describe indicator compositions which are useful in cholesterol analyses and which can be used with compounds which inhibit catalase activity yet do not substantially interfere with the assay, which patens are hereby incorporated in their entirety by reference.

Hydrogen peroxide indicator compositions generally comprise a substance having peroxidative activity, preferably peroxidase, and an indicator material which undergoes a visible change, such as a color change, in the presence of hydrogen peroxide and oxygen. Alternatively, the indicator material may be one or more substances which undergoes no substantial color change upon oxidation in the presence of hydrogen peroxide and peroxidase, but which in their oxidized form react with a color- forming or color-changing substance to give visible quantitative evidence of a chemical reaction.

A peroxidase is an enzyme which will catalyze a reaction in which hydrogen peroxide oxidizes another substance. The peroxidases are generally conjugated proteins containing iron porphyrin. Peroxidase occurs in horseradish, potatoes, fig tree sap and turnips (plant peroxidase); in milk (lacto peroxidase); and in white blood corpuscles (verdo peroxidase); as well as in some microorganisms. Certain synthetic peroxidases, such as those disclosed by Theorell and Maehyl in *Acta. Chem. Scand.*, 4: 422–434, 1950, are also satisfactory. Other substances which may be used are hemin, methemoglobin, oxyhemoglobin, hemoglobin, hemochromogen, alkaline hematin, hemin derivatives, and certain other compounds which demonstrate peroxidative or per-oxidase-like activity, namely, the ability to catalyze the oxidation of another substance by means of hydrogen peroxide and/or other peroxides. Of course, these enzymes are not stable in the presence of a great many compounds, and they should not be used with catalase inhibitors which also inhibit peroxidase activity.

Other substances which are not enzymes but which possess peroxidase-like activity include iron sulfocyanate, iron tannate, ferrous ferrocyanide, chromic salts such as potassium chromic sulfate absorbed in silica gel, etc.

The most commonly used indicators are those which exhibit a color change, such as color-forming substances which produce a color in the presence of hydrogen peroxide and peroxidase. These substances include monoamines such as aniline and its derivatives ortho-toluidine, etc.; diamines, such as ortho-phenylenediamine, N,N'-dimethylparaphenylenediamine; phenols such as phenol per se, thymol, orth-, meta- and para- cresols; alpha- and beta-naphthol; polyphenols such as catechols, guiacol, orcinol, pyrogallol, p,p-dihydroxydiphenyl and phoroglucinol; aromatic acids such as salicylic, pyrocatic and gallic acid; leuco dyes such as leucomalachite green and leucophenolphthalein; color dyes such as s 2,6-dicholorphenolindophenol; biological substances such as epinephrine, flayones, trypsine, dihydroxyphenylalanine and tryptophan; other substances such as gum guaiuca, guaiaconic acid, potassium, sodium and other water soluble iodides; and bilirubin; as well as particular dyes such as 2,2'-azine-di-[3-ethylbenzothiazoline-(6)-sulfonic acid] and 3,3'-diaminobenzidine.

In an assay for cholesterol, free cholesterol is hydrolyzed from the cholesterol esters present in the sample. Cholesterol oxidase is then added, and the action of oxygen on free cholesterol in the presence of cholesterol oxidase produces hydrogen peroxide and cholest-4-en-one. Thus, in analyzing a solution containing free cholesterol, a reagent solution containing cholesterol oxidase is used, which solution contains a suitable hydroxylamine salt substantially to reduce catalase interference. Optimum pH conditions are preferably between about 7.0 and 8.0

An indicator composition is used to quantify the amount of hydrogen peroxide generated in the oxidation. More examples of such assays are given in U.S. Pat. No. 3,983,005, to Goodhue et al., which patent is hereby incorporated in its entirety by reference.

While it is preferable that the inhibitor be sufficiently specific for catalase so as not to interfere with other enzymes used in the assay system, it is possible to first react the inhibitor with the catalase, remove the inhibitor- catalase complex, and then inactivate, if need be, residual inhibitor, prior to introducing any vulnerable enzymes into the assay system. However, since the hydroxylamine salts have been found to be relatively inert with respect to most horseradish peroxidase isoenzymes, these inhibitors are particularly useful for clinical assays which include or generate hydrogen peroxide.

The foregoing description of the specific embodiments will so fully reveal the general nature of the invention that others can, by applying current knowledge, readily modify and/or adapt for various application such specific embodiments with out departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

What is claimed is:

1. A method for analyzing biological fluid samples for the presence of an analyte other than an enzyme which decomposes hydrogen peroxide consisting essentially of:

adding to said sample an inhibitor for said enzyme, said inhibitor selected from the group consisting of hydroxylamine salts;

using hydrogen peroxide as an oxidizing agent to oxidize a dye or other intermediate to generate a detectable species; and measuring said detectable species and correlating the measurement to the amount of analyte in the sample.

2. The method according to claim 1 wherein said enzyme is selected from the group consisting of catalase, superoxide dismutase, glutathione peroxidase, and glucose-6-phosphate dehydrogenase.

3. The method according to claim 1 wherein said inhibitor is selected from the group consisting of hydroxylamine hydrochloride and hydroxylamine sulfate.

4. The method according to claim 1 wherein the detectable species is generated at least in part through the action of an exogenous enzyme reagent which is inhibited by an azide salt, and the inhibitor essentially does not inhibit said exogenous enzyme reagent.

5. The method according to claim 1 wherein said analyte is selected from the group consisting of cholesterol, triglycerides, glucose, high density lipoproteins, low density lipoproteins, uric acid, lactic acid, free fatty acids, glutamate-pyruvate transaminase, glutamate-oxaloacetate transaminase, creatine phosphokinase, lactate dehydrogenase, cholinesterase and creatinine.

6. The method according to claim 5 wherein said analyte is cholesterol.

7. The method according to claim 6 wherein cholesterol esterase or cholesterol oxidase is used as a reagent, and said inhibitor in said effective amount does not substantially inhibit cholesterol esterase or cholesterol oxidase.

8. The method according to claim 1 wherein said inhibitor is present in an amount ranging from about 0.5 to about 40 mM in the reaction solution and the reaction is conducted at a pH less than 8.0.

9. The method according to claim 1, wherein said method is conducted at a pH which is at least about 4.5 and less than 8.0.

10. The method according to claim 9, wherein the pH is at least about 7.0 and less than 8.0.

11. The method according to claim 1 wherein catalase is not added to the sample.

12. The method according to claim 1 wherein the sample contains endogenous catalase.

13. The method according to claim 3 wherein said analyte is a triglyceride.

14. The method according to claim 13 wherein said inhibitor is present in an amount ranging from about 0.5 to about 40 mM in the reaction solution and the reaction is conducted at a pH less than 8.0.

15. In a method for assaying biological samples for an analyte, which samples contain catalase, wherein said assay includes a chemical reaction using hydrogen peroxide as an oxidizing agent or using hydrogen peroxide to oxidize a dye or other intermediate to generate a detectable species which is measured and the measurements correlated to the amount of analyte in the sample, the improvement comprising adding to said sample an amount of a catalase inhibitor selected from the group consisting of hydroxylamine salts effective to substantially reduce the adverse effects of catalase in the sample on the hydrogen peroxide level.

16. The method according to claim 7 wherein in the amount of catalase inhibitor in the chemical reaction solution ranges from about 0.5 to about 40 mM.

17. The method according to claim 15 wherein said hydroxylamine salts are selected from the group consisting of hydroxylamine hydrochloride and hydroxylamine sulfate.

18. The method according to claim 15 wherein said assay is a determination of a substance selected from the group consisting of cholesterol triglycerides, glucose, high density lipoproteins, low density lipoproteins, uric acid, lactic acid, free fatty acids, glutamate-pyruvate transaminase, glutamate- oxaloacetate transaminase, creatine phosphokinase, lactate dehydrogenase, cholinesterase and creatinine.

19. The method according to claim 18 wherein said assay is a cholesterol determination.

20. The method according to claim 18 wherein said assay is a triglyceride determination.

21. The method according to claim 18 wherein said assay is a determination of high density lipoproteins.

22. The method according to claim 18 wherein said intermediate is a dye.

23. The method according to claim 15 wherein said detectable species exhibits a color change.

24. An integral analytic device for clinical assay of fluid samples comprising:

a first open reservoir;

a channel, said channel having incorporated therein an indicator composition which gives visible evidence of the presence of hydrogen peroxide and a catalase inhibitor selected from the group consisting of hydroxylamine salts in sufficient amount to minimize the adverse effects of catalase in a fluid sample to hydrogen peroxide;

and a second open reservoir.

25. The integral analytic device according to claim 24 wherein said catalase inhibitor is present in an amount ranging from about 0.5 to about 40 nM in a solution in which the clinical assay occurs.

26. The integral analytic device according to claim 24 wherein said catalase inhibitor is selected from the group consisting of hydroxylamine sulfate and hydroxylamine hydrochloride.

* * * * *